United States Patent [19]
Mori et al.

[11] Patent Number: 4,755,626
[45] Date of Patent: Jul. 5, 1988

[54] 4-ISOPROPYL-7-METHYLENE-5-CYCLO-DECEN-1-OL

[75] Inventors: Masataka Mori; Kenji Mori; Takeshi Kitahara, all of Tokyo; Koshi Koseki, Yokohama, all of Japan

[73] Assignee: Japan Tobacco, Inc., Tokyo, Japan

[21] Appl. No.: 93,547

[22] PCT Filed: Dec. 9, 1985

[86] PCT No.: PCT/JP85/00677
§ 371 Date: Aug. 7, 1987
§ 102(e) Date: Aug. 7, 1987

[87] PCT Pub. No.: WO87/03580
PCT Pub. Date: Jun. 18, 1987

[51] Int. Cl.$^4$ .............................. C07C 35/205
[52] U.S. Cl. ........................ 568/821; 568/700; 568/715; 568/828
[58] Field of Search ............ 568/819, 823, 828, 700, 568/715, 821

[56] References Cited
U.S. PATENT DOCUMENTS 3,184,432  5/1965  Wilkes et al. ............... 568/821
3,217,041 11/1965  Houlihan ..................... 568/821
3,914,315 10/1975  Miyake et al. ............... 568/821

OTHER PUBLICATIONS

Persoons et al, Tetrahedron Letters, "Sex Pheromons of the American Cockroach, *Periplanet Americana:* A Tentative Structure of Periplanone-B", 2055-2058, 1976.
Still, W. Clark, Journal of the American Chemical Society, "Periplanone-B, Total Synthesis and Structure of the Sex Excitant Pheromone of the American Cockroach", vol. 101, 2493-2495, Apr. 25, 1979.

Primary Examiner—Werren B. Lone
Attorney, Agent, or Firm—Nixon & Vanderhye

[57] ABSTRACT 4-isopropyl-7-methylene-5-cyclodecen-1-ol is disclosed. The compound allows manufacture of optically active periplanone-B on an industrial scale.

2 Claims, No Drawings

4-ISOPROPYL-7-METHYLENE-5-CYCLODECEN-1-OL

TECHNICAL FIELD

The present invention relates to 4-isopropyl-7-methylene-5-cyclodecen-1-ol, which is useful as an intermediate for synthesizing periplanone-B which is a sex pheromone of American cockroaches.

BACKGROUND ART

Periplanone-B is the main component of the sex pheromone of female American cockroaches (Periplaneta americana) which are a type of harmful insect distributed worldwide. C. J. Persoons et al. were the first to isolate this component and determine its plane structure, and they reported that this component had a specific germacrene-type sesquiterpenoid structure (C. J. Persoons et al., Tetrahedron Letters, 24, 2055 (1976)). According to Persoons et al., periplanone-B produces a very strong physiological effect; 1 picogram (1/100,000,000,000 gram) of this component attracts and sexually excites male American cockroaches. W. C. Still et al. synthesized a racemic material of periplanone-B and determined its relative configuration (W. C. Still, J. Am. Chem. Soc., 101, 2495 (1979)). K. Nakanishi et al optically resolved the racemic material synthesized by Still et al. and determined the absolute configuration of periplanone-B by a spectroscopic method (K. Nakanishi et al., J. Am. Chem. Soc., 101, 2495 (1979)). S. N. Schreiber reported another method of synthesizing periplanone-B in J. Am. Chem. Soc., 106, 4038 (1984).

As has been described above, periplanone-B is a sex pheromone of American cockroaches and can be used to attract or trap male American cockroaches in a specific location. However, insects including American cockroaches produce only a small amount of sex pheromone, and extraction thereof is not practical. Therefore, development of a method which allows synthesis of periplanone-B on an industrial scale is desirable.

In the synthetic methods of Still et al. and Schreiber et al., the starting material is a racemic material (ethoxyethyl ether of (+)-5-(hydroxymethyl)cyclohexenone in the former, and (+)-4-isopropyl-2-cyclohexen-1-one in the latter). Therefore, periplanone-B obtained as a final product in either method is only a racemic material. A starting material racemic material used in either method is very difficult to optically resolve, and requires a complex process therefor. In addition, these methods use oxy-Cope rearrangement, which cannot be performed on a large scale, in the formation of a 10-membered ring, which is a key reaction in the synthesis of periplanone-B. These methods are not, therefore, efficient. Moreover, these methods include many steps which require fine adjustment of reaction conditions, such as organometallic reactions or stereoselective reactions.

DISCLOSURE OF INVENTION

It is, therefore, an object of the present invention to provide an optically active intermediate which allows synthesis of optically active periplanone-B on an industrial scale.

There is provided according to the present invention 4-isopropyl-7-methylene-5-cyclodecen-1-ol.

BEST MODE OF CARRYING OUT THE INVENTION

The compound according to the present invention, i.e., 4-isopropyl-7-methylene-5-cyclodecen-1-ol is represented by the following formula:

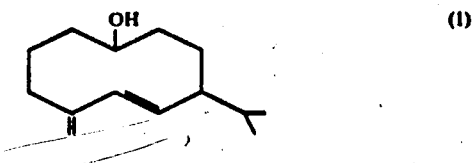

This compound can be manufactured using, as a starting material, optically active d-dihydrolimonene, which is known per se and is readily available, following the reaction route below:

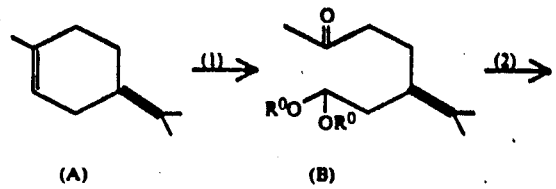

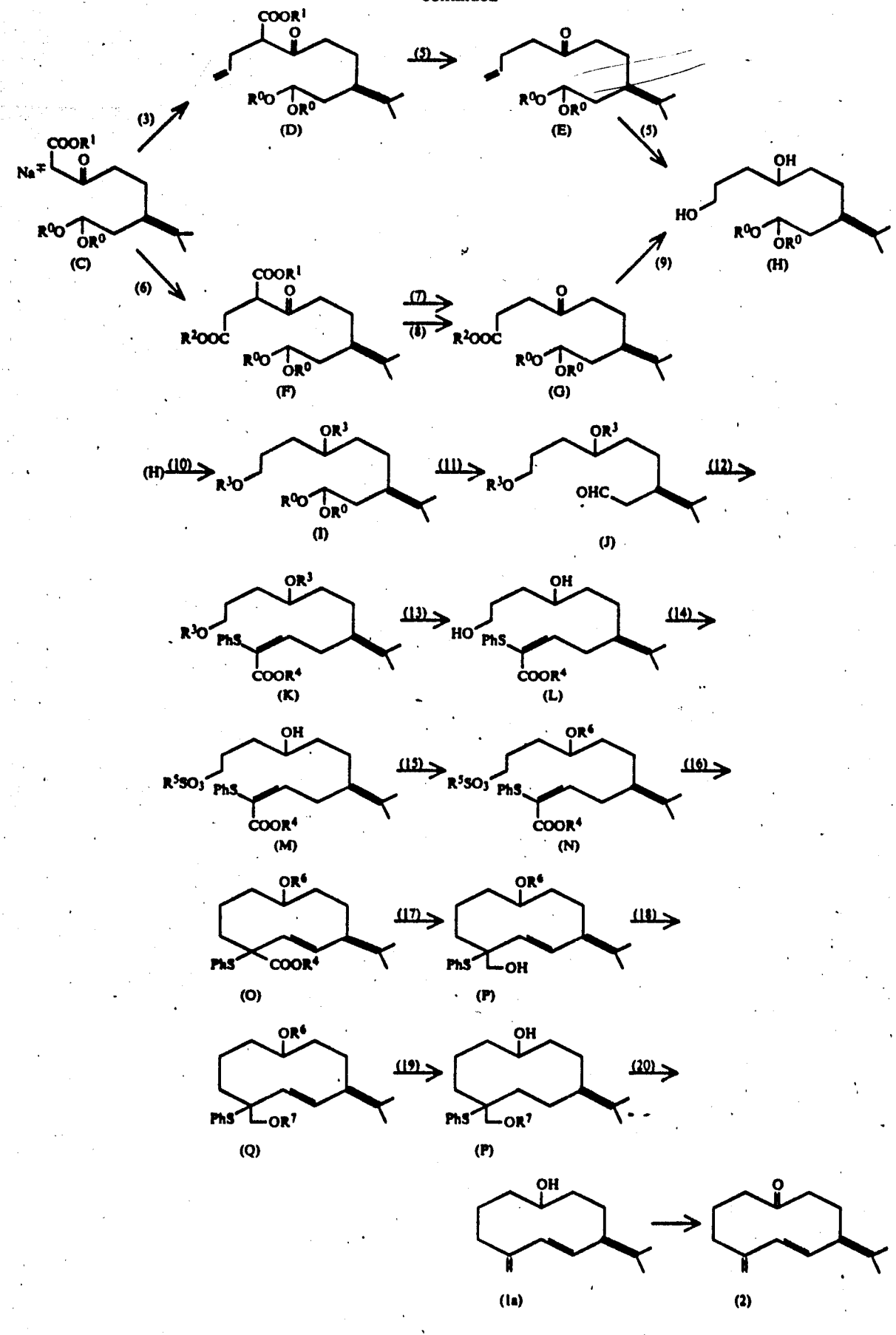

A method of manufacturing the compound of the invention will be described below, along the above route.

(i) In step 1, d-dihydrolimonene, represented by formula A, is subjected to ozonolysis, and resulting ozonolysed product is reduced with dimethylsulfide. The ozonolysis can be performed by suspending d-dihydrolimonene in an alcohol solvent, and passing ozone through the suspension at a temperature of 0° C. or lower, and preferably −30° C. or lower. The alcohol solvent can be an alcohol such as methanol, ethanol, or ethylene glycol, or a mixture thereof with methylene chloride or chloroform. A preferred solvent is a mixture of methanol with methylene chloride. Ozone is contained in oxygen or air at a concentration of 1 to 10% by volume, and the resultant gas is passed through the suspension. The ozonolysis is normally completed within 5 to 10 hours.

The reduction can be performed by adding dimethylsulfide, together with an acid catalyst such as hydrochloric acid, sulfuric acid, or para-toluene sulfonic acid, to the reaction mixture and allowing the resultant reaction mixture to react at a temperature of −60° C. or lower, and then at 0° C. to 30° C. Normally, dimethylsulfide is added in an amount of 2 to 3 equivalents per equivalent of d-dihydrolimonene, and the acid catalyst is added in an amount of 0.05 to 0.1 equivalents per equivalent of d-dihydrolimonene.

These ozonolysis and reduction provide (3R)-3-isopropyl-6-oxoheptanal dialkylacetal, represented by formula B. An alkyl group, $R^0$, in formula B is introduced as a result of the reaction of ozonolysed product with the alcohol used as the solvent. The compound of formula B can be purified by vacuum distillation, and can be normally obtained at a yield of 90 to 95%.

(ii) In step 2, the compound of formula B is allowed to react (Claisen condensation) with dialkyl carbonate or alkyl chloroformate in the presence of sodium hydride in an ether solvent, at 50° C. to 120° C., under the stream of an inert gas such as nitrogen or argon. Dialkyl carbonate or alkyl chloroformate used herein is normally one in which each alkyl group has 1 to 3 carbon atoms. Dimethyl carbonate is preferably used. The ether solvent can be an ether such as diethyl ether, tetrahydrofuran (THF), dioxane, or dimethoxyethane (DME); a mixture of dioxane with methanol; a mixture of dioxane, methanol, and dimethylformamide (DMF); or a mixture of benzene with diethyl ether. Sodium hydride is used in an amount of 2 equivalents per equivalent of the compound of formula B, and dialkyl carbonate or alkyl chloroformate is used in an amount of 1 to 5 equivalents, and preferably 3 equivalents 1, per equivalent of the compound of formula B.

Upon this reaction, (6R)-alkyl-6-isopropyl-9,9-dialkoxy-3-oxooctanoate, represented by formula C, is obtained in the form of a sodium salt in the solution. The alkoxycarbonyl group, —COOR$^1$, in the compound of formula C, is derived from dialkyl carbonate or alkyl chloroformate. The sodium salt of the compound of formula C is used in the next step, without separation.

In order to manufacture the compound represented by formula H from the compound represented by formula C, one of the following two methods (iii-a) and (iii-b) can be used:

(iii-a) In step 3, an allyl halide (e.g., allyl chloride or allyl bromide) is added to the solution of the sodium salt of the compound of formula C obtained in step 2, in an amount of 1 to 2 equivalents, and preferably 1.1 equivalent, per equivalent of the compound of formula C, and the mixture is allowed to react at 50° C. to 120° C., for 1 to 5 hours to obtain (2RS,7R)-alkyl-7-isopropyl-9,9-dialkoxy-3-alkoxycarbonyl-4-oxononanoate, represented by formula D.

In step 4, without purification, the compound of formula D is heated together with an alkali metal hydroxide (lithium hydroxide, sodium hydroxide, or potassium hydroxide) in a mixed solvent of water and alcohol, preferably a water-methanol solvent mixture, at 60° C. to 100° C., for 1 to 3 hours, to perform saponification/decarboxylation. The alkali metal hydroxide is used in an amount of 3 to 5 equivalents per equivalent of the compound of formula D. Upon this reaction, (8R)-8-isopropyl-10,10-dialkoxy-1-decene-5-one, represented by formula E, is obtained. This compound can be purified by vacuum distillation. The compound of formula E is normally obtained at a yield of 65 to 85%.

In step 5, the compound of formula E is oxidized, and the resultant oxidized product is reduced to provide (5R,8RS)-6,9-dihydroxy-3-isopropylnonanaldialkylacetal, represented by formula H. The oxidation of the compound of formula E can be performed in a two-phase solvent consisting of diethyl ether and water, at 0° C. to 30° C. for 3 to 5 hours, using, as an oxidizing agent, 2 to 5 equivalents, and preferably 3 equivalents, of potassium permanganate; a mixture of 0.01 to 1 equivalent, and preferably 0.1 equivalents, of potassium permanganate with 2 to 5 equivalents, and preferably 3 equivalents, of sodium periodate; or a mixture of 0.1 to 1 equivalent, and preferably 0.1 equivalents, of osmium tetraoxide with 2 to 5 equivalents, and preferably 3 equivalents, of sodium periodate, per equivalent of the compound of formula E, respectively. The resultant oxidized product is used for the next step, without purification.

The reduction of the oxidized product is performed in an ether solvent at 0° C. to 10° C., for 1 to 3 hours, using lithium aluminum hydride as a reducing agent in an amount of 1 to 2 equivalents, and preferably 1.2 equivalents, per equivalent of the oxidized product.

(iii-b) In step 6, alkyl bromoacetate, preferably methyl bromoacetate, is added to the solution of sodium salt of the compound of formula C obtained in step 2, in an amount of 1 to 2 equivalents, and preferably 1.1 equivalents, of the sodium salt, and the reaction mixture is allowed to react at 50° C. to 120° C., for 1 to 5 hours to provide (3RS,7R)-alkyl-7-isopropyl-9,9-dialkoxy-3-alkoxycarbonyl-4-oxononanoate, represented by formula F. The alkoxycarbonyl group, —COOR$^2$, in formula F is derived from the alkyl bromoacetate used.

In step 7, the compound of formula F is, without purification, saponified/decarboxylated by the procedures in step 4 and is treated with diazomethane, or is treated with an alcohol (e.g., methanol) in the presence of an acid catalyst (e.g., para-toluene sulfonic acid) to provide (7R)-alkyl-6-isopropyl-9,9-dialkoxy-4-oxononanoate, represented by formula G. Diazomethane is used in an amount of 1 to 2 equivalents per equivalent of the compound of formula F. The alcohol and acid catalyst are used in an amount of 3 to 5 equivalents and 0.05 to 0.1 equivalents, respectively, per equivalent of the compound of formula F. The yield of the compound of formula G in this method is normally 70 to 80%.

Alternatively, the compound of formula G can be converted in one step from the compound of formula F to the compound of formula G. More specifically, in step 8, the compound of formula F is heated together with a dealkoxycarbonylating agent (sodium chloride, sodium cyanide or sodium cyanide) in a solvent mixture of dimethylsulfoxide (DMSO) and water at 100° C. to 150° C., for 3 to 5 hours, to perform dealkoxycarbonylation (i.e., elimination of the —COOR$^1$ group at the 3-position). The dealkoxycarbonylating agent is used in an amount of 0.5 to 1 equivalent per equivalent of the compound of formula F. This reaction yields the compound of formula G. The compound of formula G is normally obtained by this reaction with a yield of 60 to 70%.

Subsequently, in step 9, the compound of formula G is reduced at 0° C. to 20° C., for 1 to 2 hours, using lithium aluminum hydride in an amount of 1 to 2 equivalents per equivalent of the compound of formula G.

The preparation of the compound of formula H from the compound of formula C is preferably performed via steps 3, 4, and 5. This method is more suitable for industrial manufacture of the compound of formula H.

(iv) In step 10, the two hydroxyl groups of the compound of formula H are acylated using an acylating agent (a carboxylic acid anhydride, preferably acetic anhydride; or an acyl chloride, preferably acetyl chloride). The acylating agent is used in an amount of 1.5 to 5 equivalents per equivalent of the compound of formula H. The acylation is performed at 20° C. to 50° C., for 4 to 15 hours. This reaction yields the compound of formula I. In formula I, each $R^3$ is an acyl group. The compound of formula I is used in the next step, without isolation.

(v) In step 11, the compound of formula I is treated with a strong acid (e.g., hydrochloric acid, sulfuric acid, or perchloric acid; preferably hydrochloric acid) at −10° C. to 20° C., for 5 minutes to 1 hour. The strong acid is used in an amount of 2 to 4 equivalent per equivalent of the compound of formula I. This treatment yields the compound of formula J.

(vi) In step 12, the compound of formula J is condensed with an alkyl phenylthioacetate, preferably methyl phenylthioacetate, under the stream of an inert gas such as nitrogen or argon, in an ether solvent such as diethyl ether, tetrahydrofuran, or dimethoxyethane, in the presence of a base catalyst. The base catalyst can be n-butyl lithium, lithium diisopropylamide, or sodium hydride. The preferred catalyst is lithium diisopropylamide. The base catalyst is used in an amount of 1 to 1.5 equivalents per equivalent of the compound of formula J. The condensation temperature is −60° C. to −10° C., and the condensation time is 10 minutes to 1 hour. Thus, (5R,8RS,2EZ)-alkyl-8,11-diacyloxy-5-isopropyl-2-phenylthio-2-undecenoate, represented by formula K, is obtained. In formula K, Ph represents phenyl group, and the alkoxycarbonyl group, —COOR$^4$, is derived from the alkyl acetate moiety of the alkyl phenylthioacetate used.

(vii) In step 13, the compound of formula K is allowed to react with an alkali metal alkoxide in an alcohol, e.g., methanol, at room temperature to 50° C., to perform deacylation. The alkali metal alkoxide can be lithium alkoxide, sodium alkoxide, or potassium alkoxide, preferably sodium methoxide. The alkoxide is used in an amount of 1 to 3 equivalents per equivalent of the compound of formula K. This deacylation yields (5R,8RS,2EZ)-alkyl-8,11-dihydroxy-5-isopropyl-2-phenylthio-2-undecenoate, represented by formula L.

(viii) In step 14, the compound of formula L is allowed to react with para-toluenesulfonyl chloride or alkanesulfonyl chloride, preferably para-toluenesulfonyl chloride, in methylene chloride or chloroform at 0° C. or lower, preferably −15° C. or lower, in the presence of dimethylaminopyridine and triethylamine or pyridine. Triethylamine or pyridine is used in an amount of 2 to 4 equivalents per equivalent of the compound of formula L, and dimethylaminopyridine is used in an amount of 0.1 to 0.3 equivalents per equivalent of the compound of formula L. Para-toluenesulfonyl chloride or alkanesulfonyl chloride is used in an amount of 1.5 to 3 equivalents per equivalent of the compound of formula L. This reaction regio-selectively alkylsulfonylates the hydroxyl group at the 11-position in the compound of formula L, and provides the compound represented by formula M. In formula M, $R^5$ represents an alkyl group and is derived from the sulfonylation agent.

(ix) In step 15, the compound of formula M is reacted with dihydropyran or ethyl vinyl ether, in methylene chloride or chloroform at 0° C. to 20° C., using para-toluenesulfonic acid or pyridinium para-toluene sulfonate as a catalyst. The catalyst is used in an amount of 0.05 to 0.1 equivalents per equivalent of the compound of formula M. Dihydropyran or ethyl vinyl ether is used in an amount of 1.2 to 5 equivalents per equivalent of the compound of formula M. This reaction is completed within 1 to 4 hours. Upon this reaction, the hydroxyl group at the 8-position in the compound of formula M is protected by an acetal protective group, and (5R,8RS,2EZ)-alkyl-5-isopropyl-2-phenylthio-8-alkoxy-11-alkylsulfonyloxy-2-undecenoate, represented by formula N, is obtained. In formula N, $R^6$ is an alkyl group and is derived from the acetal protective group.

(x) In step 16, the compound of formula N is heated and cyclized in an ether solvent, e.g., tetrahydrofuran, diethyl ether, dimethoxyethane, or diglyme, or an aromatic solvent, e.g., benzene or toluene, at room temperature to 100° C., preferably 70 to 90° C., under the stream of an inert gas such as nitrogen or argon, in the presence of a base catalyst. The solvent used in this step is preferably dimethoxyethane. The base catalyst can be a diisopropylamide or bistrimethylsilylamide of lithium, sodium, or potassium, or n-butyl lithium and 1,4-diazabicyclo [2,2,2]octane, and is preferably sodium bistrimethylsilylamide. The basic catalyst is used in an amount of 1.2 to 1.5 equivalents per equivalent of the compound of formula N. The cyclization can be performed within 30 minutes to 1 hour. In this manner, a 10-membered ring compound represented by formula O and having a trans double bond in the ring, i.e., (1RS,2E,4S,7RS)-alkyl-4-isopropyl-1-phenylthio-7-tetrahydropyranyloxy-2-cyclodecenecarboxylate, is obtained. This cyclization has excellent efficiency, and a yield of the cyclized product is 60 to 70%.

(xi) In step 17, the alkoxycarbonyl group, —COOR$^4$, in the compound of formula O is reduced and converted into hydroxyl group. More specifically, the compound of formula O is allowed to react with a reducing agent, i.e., lithium aluminum hydride, in an ether solvent, e.g., diethyl ether, at −10° C. to 10° C., for 0.5 to 2 hours. The reducing agent is used in an amount of 1.2 to 2 equivalents per equivalent of the compound of formula O. This reduction substantially quantitatively yields the compound of formula P.

(xii) In step 18, the compound of formula P is allowed to react with an acylating agent, in tetrahydrofuran, in the presence of dimethylaminopyridine and pyridine or triethylamine. The acylating agent can be benzoyl chloride, p-methoxy benzoyl chloride, or acetic anhydride, and is used in an amount of 1 to 5 equivalents per equivalent of the compound of formula P. The acylation is performed at 0° C. to 30° C. for 5 to 10 hours. This acylation provides the compound of formula Q. In formula Q, $R^7$ is an acyl group.

(xiii) In step 19, the acylated product represented by formula Q is treated with an acid catalyst, e.g., acetic acid, hydrochloric acid, sulfuric acid, or an acidic ion-exchange resin (e.g., "Dowex 50W" (H+ type) available from Dow Chemical Co.), in an alcohol or an alcohol-water solvent mixture at 20° C. to 50° C., so as to remove the acetal protective group. The acid catalyst is used in an amount of 0.05 to 0.5 equivalents per equivalent of the compound of formula Q. The treatment with the acid catalyst can be performed within 1 to 5 hours. Upon this treatment, (1RS,2E,4S,7RS)-7-hydroxy-4-isopropyl-1-phenylthio-2-cyclodecene-1-alkanol carboxylate ester, represented by formula R, is obtained.

(xiv) In step 20, the compound of formula Q is allowed to react with a reducing agent under the stream of an inert gas such as nitrogen or argon. This reduction can be performed in one of the three following methods: In a first method, an alkali metal (e.g., metallic lithium, sodium, or potassium) and naphtalene are used as a reducing agent, and the reduction is performed in an ether solvent, e.g., diethyl ether, tetrahydrofuran, or dimethoxyethane at −70° C. or lower. The alkali metal is used in an amount of 5 to 10 equivalents per equivalent of the compound of formula Q, and naphthalene is used in an amount of 5 to 10 equivalents per equivalent of the compound of formula Q.

In a second method, an alkali metal (metallic lithium, sodium, or potassium) is used, and the reduction is performed in liquid ammonia at −30° C. or lower. The alkali metal is used in an amount of 5 to 10 equivalents per equivalent of the compound of formula Q.

In a third method, an amalgam of an alkali metal (metallic lithium, sodium, or potassium) with mercury is used as a reducing agent, and the reduction is performed in tetrahydrofuran at −0° C. or lower. The amalgam is used in an amount of 5 to 10 equivalents per equivalent of the compound of formula Q.

The first method is preferred. When the first method is used, sodium is most preferably used as the alkali metal.

Upon this reduction, the phenylthio group and acyloxy group are eliminated from the compound of formula R so as to provide the compound according to the present invention, represented by formula 1a, i.e., (1RS,4S,5E)-4-isopropyl-7-methylene-5-cyclodecen-1-ol.

When the compound of the present invention is allowed to react with an oxidizing agent in methylene chloride or chloroform at 0° C. to room temperature for 0.5 to 5 hours, (4S,5E)-4-isopropyl-7-methylene-5-cyclodecen-1-one (formula 2) is obtained which is an optically active substance of an intermediate product obtained in synthesis of a racemic material by Schreiber et al., as described above. The oxidizing agent can be a mixture of chromic anhydride and pyridine; a mixture of pyridinium chlorochromate and Molecular Sieves; pyridinium dichromate; or a mixture of dimethylsulfoxide and oxalyl chloride. The oxidizing agent is used in an amount of 2 to 8 equivalents per equivalent of the compound of formula 1.

Optically active periplanone-B represented by the following formula:

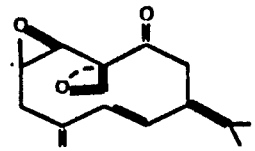

can be manufactured from the compound of formula 2 in accordance with the method of Schreiber et al.

Stated briefly, the compound of formula 2 is treated with lithium diisopropylamide or lithium bistrimethylsylilamide in an ether solvent under the stream of an inert gas such as nitrogen or argon, so as to be enolized. Subsequently, the resultant product is sulfenylated with diphenyldisulfide or phenylthiobenzenesulfonate to provide (4S,5E)-4-isopropyl-7-methylene-10-phenylthio-5-cyclodecen-1-one. This compound is oxidized by (i) sodium periodate or hydrogen peroxide in a water-alcohol solvent mixture at room temperature or (ii) m-perchlorobenzoic acid in a chlorinetype solvent at a temperature of −20° C. or lower to provide a sulfoxide compound, (4S,5E)-4-isopropyl-7-methylene-10-phenylsulfinyl-5-cyclodecen-1-one.

The sulfoxide compound is dissolved in an aromatic solvent, e.g., benzene, toluene, or xylene, preferably toluene, and is heated at 50° to 150° C. in the presence of calcium carbonate, pyridine, or trimethylphosphite. Upon heating, the sulfoxide group is decomposed to provide (8S,2Z,6E)-8-isopropyl-5-methylene-2,6-cyclodecadien-1-one.

The decomposition product is allowed to react with t-butylperoxide of an alkali metal, preferably, potassium t-butylperoxide in an ether solvent, e.g., diethyl ether, tetrahydrofuran, or dimethoxyethane, preferably, tetrahydrofuran, at 0° C. to room temperature under the stream of an inert gas such as nitrogen or argon so as to stereoselectively epoxidate the enone moiety. This reaction yields an epoxide, (4S,5E,9R,10R)-9-epoxy-4-isopropyl-7-methylene-5-cyclodecen-1-one.

The epoxide is allowed to react with lithium diisopropylamide or lithium bistrimethylsilylamide in an ether solvent such as diethyl ether, tetrahydrofuran, or dimethoxyethane, preferably, tetrahydrofuran, under the stream of an inert gas such as argon, thereby obtaining an enolate. The enolate is allowed to react with phenyl selenyl bromide to obtain a selenide compound.

The selenide compound is oxidized with hydrogen peroxide in water-tetrahydrofuran to provide a seleno oxide compound, (4S,5E,9R,10R)-9-epoxy-4-isopropyl-7-methylene-2-phenylselenenyl-5-cyclodecen-1-one.

The seleno oxide compound is treated with acetic anhydride-sodium acetate in tetrahydrofuran or tetrahydrofuran-pyridine so as to allow a selenapunmellar rearrangement to occur and to prepare a acetoxyselenide. When the acetoxyselenide is hydrolyzed with water and potassium carbonate, an α-diketone compound, (3S,4E,8R,9R)-8-epoxy-3-isopropyl-6-methylene-10-oxo-4-cyclodecen-1-one is obtained.

Finally, when the α-diketone compound is allowed to react with dimethyl sulfonium methylide in an ether solvent, e.g., diethyl ether, tetrahydrofuran, or dimethoxyethane, preferably, a mixture of tetrahydrofuran and dimethylsulfoxide, under the stream of an inert gas such as nitrogen or argon, only one ketone is regio-selectively epoxidated to provide optically active periplanone-B represented by formula 3.

EXAMPLE 1

SYNTHESIS OF (1RS,4S,5E)-4-isopropyl-7-methylene-5-cyclodecen-1-ol (1) 200 g of d-dihydrolimonene were suspended in a mixture of 800 ml of methanol and 200 ml of methylene chloride. While the temperature of the suspension was kept at −30° C. in a dry ice-acetone bath, oxygen gas containing 5% of ozone was passed through the suspension under vigorous agitation for about 6 hours, to perform ozonolysis. After the ozonolysis was terminated, nitrogen gas was passed through the reaction mixture to expell the excess ozone.

After cooling the reaction mixture to −60° C., a suspension of 300 ml of dimethylsulfide and 20 g of para-toluenesulfonic acid in 100 ml of methanol, was added gradually to the mixture. After allowing the reaction mixture to react at −60° C. for about 2 hours under agitation, the temperature of the mixture was elevated to about room temperature over about 2 hours, and the mixture was then kept stirred overnight. Thereafter, the mixture was neutralized with a saturated-sodium carbonate aqueous solution and was concentrated under reduced pressure to a volume of about 300 ml. Then, 300 ml of water were added to the concentrate, and the mixture was extracted three times, each time with 400 ml of diethyl ether. The ether layers were combined and washed with 200 ml of water three times and once with 100 ml of a saturated sodium chloride aqueous solution, dried over anhydrous magnesium sulfate, and filtered. The ether was removed from the filtrate under reduced pressure to obtain 299 g of a crude product, which was subjected to vacuum distillation (99° C./1.6 mmHg), to provide 288 g of purified (3R)-3-isopropyl-6-oxoheptanal dimethylacetal (the compound of formula B, wherein each $R^0$ is methyl group). The yield was 92%.

Analysis Results:
Boiling point: 99° C./1.6 mmHg.
Infrared spectrum ($cm^{-1}$): 2980, 2900, 2850, 1740, 1720, 1470, 1440, 1390, 1370, 1255, 1195, 1165, 1125, 1055, 965, 910.
NMR spectrum ($\delta$, ppm): 4.31 (t, J=5.5 Hz, H-7), 3.20 (s, 5H, -O-methyl), 2.32 (dd, J=5, 6 Hz, 1H, H-9), 2.05 (s, 3H, H-1), 1.8-1.0 (6H), 0.85 (d, J=6.5 Hz, 6H, isopropylmethyl).

(2-a-1) 25 g of sodium hydride were suspended in 500 ml of dry dioxane under argon gas stream, and 143 g of dimethyl carbonate and 3.6 ml of methanol were added to the suspension, which was then stirred under reflux. A solution of 114 g of the product in step 1, in 90 ml of dry dioxane, was added to the mixture over 4 hours, and the resultant mixture was stirred overnight under reflux. Upon this reaction, (3R)-3-isopropyl-6-oxoheptanal dimethylacetal was converted into a sodium salt of (6R)-methyl 6-isopropyl-8,8-dimethoxy-3-oxooctanoate, a Claisen condensate.

(2-a-2) 72 g of allyl bromide were added to the reaction mixture of step 2-a-1, over 30 minutes, and the resultant mixture was allowed to react under reflux for 1.5 hours. After reaction, the reaction mixture was cooled to room temperature, was poured onto 100 g of ice, and was concentrated under reduced pressure to remove dioxane. The concentrate was extracted twice, each time with 200 ml of diethyl ether, and the ether was removed under reduced pressure to provide 168 g of a crude product, (2RS,7R)-methyl 7-isopropyl-9,9-dimethoxy-3-methoxycarbonyl-4-oxononanoate.

The crude product was added to a solution of 45 g of potassium hydroxide in 800 ml of water and 550 ml of methanol, and was allowed to react under reflux for 1.5 hours. The reaction mixture was cooled to room temperature, and was extracted 6 times, each time with 200 ml of diethyl ether. The ether phases were combined and washed with 100 ml of a saturated sodium chloride aqueous solution, evaporated to dryness, and distilled under reduced pressure (128°-130° C./0.35 mmHg). In this manner, 111 g of purified (8R)-8-isopropyl-10,10-dimethoxy-1-decen-5-one (the compound of formula E, wherein each $R^0$ is a methyl group) were obtained. The yield was 82%.

Analysis Results:
Infrared spectrum ($cm^{-1}$): 3100, 2975, 2900, 2850, 1715, 1645, 1465, 1440, 1415, 1390, 1370, 1250, 1195, 1125, 1075, 1050, 1000, 960, 915, 820.
NMR spectrum ($\delta$, ppm): 5.7 (m, 1H, H-2), 4.95 (m, 2H, H-1), 4.32 (t, J=6 Hz, 1H, H-10), 3.20 (s, 6H, -O-methyl), 2.6-2.0 (6H, H-3, 4, 6), 1.9-1.0 (6H), 0.85 (d, J=6.5 Hz, 6H, isopropyl-methyl).

(2-a-3) 6.2 g of osmium tetraoxide and 327 g of sodium periodate were suspended in a mixture of 1 liter of diethyl ether and 1.5 liters of water. Then, 111 g of the product of step 2-a-2 were added to the suspension, and the resultant mixture was stirred at room temperature for 4 hours. The ether phase was separated, and the aqueous phase was extracted three times, each time with 200 ml of diethyl ether. All the ether phase was collected, washed with a saturated sodium chloride aqueous solution, dried over anhydrous magnesium sulfate, and evaporated to dryness to provide 160 g of an oily product.

After dissolving the oily product in 300 ml of dry diethyl ether, it was added dropwise at −10° C. or less under agitation, over 1.5 hours, to a ice-cooled suspension of 23.5 g of lithium aluminum hydride in 800 ml of dry diethyl ether. After adding 30 ml of a 15% sodium hydroxide aqueous solution to the mixture, the resultant mixture was filtered through a Buchner funnel packed with celite, and the precipitate was washed with tetrahydrofuran. All the filtrate was collected, and concentrated under reduced pressure to provide 154 g of a crude product, (5R,8RS)-6,9-dihydroxy-3-isopropyl-nonanal dimethylacetal (the compound of formula H, wherein each $R^0$ is methyl group).

Without purification, the crude product was dissolved in a mixture of 100 ml of acetic anhydride and 300 ml of pyridine, and the resultant mixture was allowed to react under agitation overnight. The pyridine was distilled off the reaction mixture, under reduced pressure. The residue was poured into a mixture of 100 ml of concentrated hydrochloric acid and 200 g of ice, and the resultant mixture was stirred for 5 minutes and was extracted with 300 ml of ether. After the ether phase was sequentially washed with water, a saturated sodium bicarbonate aqueous solution, and a saturated sodium chloride aqueous solution, it was dried over anhydrous magnesium sulfate and evaporated to dryness to provide 148 g of the compound of formula J wherein each $R^3$ is methyl group. The yield was 80%.

Analysis Results:
Infrared spectrum ($cm^{-1}$): 3000, 2910, 2750, 1460, 1390, 1375, 1245, 1025, 970.
NMR spectrum ($\delta$, ppm): 9.79 (brs, 1H, H-1), 4.8 (m, 1H, H-6), 3.98 (m, 2H, H-9), 2.25 (m, 2H, H-2), 1.98 (s, 6H, -acetyl-methyl), 1.8-1.2 (10H), 0.85 (2d, J=6.5 Hz, 6H, isopropyl-methyl).

(2-b-1-i) 47 g of sodium hydride were suspended in 660 ml of dry dioxane under argon gas stream. Then, 150 ml of dimethyl carbonate were added to the suspension and the mixture was stirred under reflux. A solution of 126 g of the product of step 1, in 100 ml of dry dioxane, was added dripwise to the mixture over 4 hours, and the resultant mixture was stirred under reflux overnight. A solution of 64 ml of methyl bromoacetate in 60 ml of DMF was added dropwise to the reaction mixture over 30 minutes, and this mixture was stirred under reflux for 1.5 hours. After cooling the reaction mixture to room temperature, it was poured onto 100 g of ice and was directly concentrated under reduced pressure to remove dioxane. The residue was extracted twice, each time with 300 ml of ether. The ether phase was combined, sequentially washed with water and a saturated sodium chloride aqueous solution, dried over anhydrous sodium sulfate, and evaporated to dryness to provide 207 g of a crude product, (3RS,7R)-methyl 7-isopropyl-9,9-dimethoxycarbonyl-4-oxononanoate (the compound of formula F, wherein each of $R^0$, $R^1$, and $R^2$ is methyl group).

The crude product, without purification, was added to a solution of sodium hydroxide in 900 ml of water and 600 ml of methanol, and was allowed to react under reflux, for 1.5 hours. Thereafter, the reaction mixture was cooled to room temperature, was adjusted to a pH of 6, using a 1N hydrochloric acid, while being cooled with ice, and was extracted 6 times, each time with 200 ml of ether. The ether phases were combined, washed with a saturated sodium chloride aqueous solution, and evaporated to dryness. The evaporation to dryness was conducted after addition of 200 ml of benzene, twice. The residue was dissolved in 500 ml of dry diethyl ether, and a solution of diazomethane in diethyl ether was added to the resultant solution, while being cooled with ice, until the color of diazomethane did not disappear. Acetic acid was added to the reaction mixture until the color of the diazomethane disappeared, so as to decompose excess diazomethane. The mixture was then sequentially washed with water, a saturated sodium bicarbonate aqueous solution, and a saturated sodium chloride aqueous solution, was dried over anhydrous sodium sulfate, and was evaporated to dryness to provide 121 g of (7R)-methyl 6-isopropyl-9,9-dimethoxy-4-oxononanoate (the compound of formula G, wherein each of $R^0$ and $R^2$ is methyl group). The yield was 72%.

Analysis Results:
Infrared spectrum (cm$^{-1}$): 2980, 2900, 2850, 1745, 1725, 1670, 1470, 1440, 1390, 1375, 1200, 1170, 1130, 1060, 965, 910.
NMR spectrum (δ, ppm): 4.30 (t, J=5.5 Hz, H-9), 3.58 (s, 3H, ester-O-methyl), 3.17 (s, 6H, acetal-O-methyl), 2.6-2.1 (6H, H-2, 3, 5), 1.7-1.1 (6H), 0.85 (d, J=6.5 Hz, 6H, isopropyl-methyl).

(2-b-1-ii) After suspending 20 g of sodium hydride in 200 ml of dry dioxane under argon gas stream, 60 ml of dimethyl carbonate were added to the suspension, which was stirred under reflux. A solution of 48 g of the product of step 1, in 50 ml of dry dioxane, was added to the mixture over 4 hours, and the resultant mixture was further stirred under reflux overnight. A solution of 30 ml of methyl bromoacetate in 30 ml of DMF was added to the reaction mixture over 30 minutes, and this mixture was stirred under reflux, for 1.5 hours. After the reaction mixture was cooled to room temperature, it was poured onto 100 g of ice and was concentrated under reduced pressure to remove dioxane. The residue was extracted twice, each time with 100 ml of diethyl ether, and the ether phases were combined. The combined ether phase was sequentially washed with water and a saturated sodium chloride aqueous solution, was dried over anhydrous magnesium sulfate, and was evaporated to dryness to provide 37 g of a crude product, (3RS,7R)-methyl 7-isopropyl-9,9-dimethoxy-3-methoxycarbonyl-4-oxononanoate.

Without purification, the crude product was added to a mixture of 6 g of sodium chloride, 5 ml of water, and 60 ml of dimethylsulfoxide, and the resultant mixture was thereafter stirred under reflux, for 4 hours. After the reaction mixture was left to cool, 50 ml of water were added, and this mixture was extracted twice, each time with 100 ml of diethyl ether. The ether phases were combined, washed with water three times, and washed with a saturated sodium chloride aqueous solution, dried over anhydrous magnesium sulfate, and evaporated to dryness to provide 42 g of (7R)-methyl 6-isopropyl-9,9-dimethoxy-4-oxononanoate. The yield was 65%. This compound provided the same analysis results as the compound obtained in step (2-b-1-i).

(2-b-2) 120 g of (7R)-methyl 6-isopropyl-9,9-dimethoxy-4-oxononanoate obtained above were dissolved in 100 ml of dry diethyl ether. The solution was added dropwise over 30 minutes under agitation at 10° C., to an ice-cooled suspension of 18 g of lithium aluminum hydride in 900 ml of dry ethyl ether. After adding 10 ml of a 15% sodium hydroxide aqueous solution to the mixture, the resultant mixture was filtered through a Buchner funnel packed with celite, and the precipitate was washed with tetrahydrofuran. All of the filtrate was combined, and concentrated under reduced pressure to obtain 93 g of a crude product (5R,8RS)-6,9-dihydroxy-3-isopropylnonanal dimethylacetal (the compound of formula H, wherein each $R^0$ is methyl group). The yield was 95%.

Without purification, the crude product was dissolved in a mixture of 150 ml of acetic anhydride and 1.2 liters of pyridine, and the solution was allowed to react under agitation overnight. Pyridine was removed from the reaction mixture under pressure, and the residue was charged into a mixture of 100 ml of concentrated hydrochloric acid and 100 g of ice. The resultant mixture was stirred for 5 minutes and was extracted twice, each time with 200 ml of ether. The ether phase was sequentially washed with water, a saturated sodium bicarbonate aqueous solution, and a saturated sodium chloride aqueous solution, was dried over sodium sulfate, and was evaporated to dryness to provide 92 g of the compound of formula J, wherein each $R^3$ is acetyl group. The yield was 95%. The compound provided the same analysis results as those of the product obtained in step (2-a-3).

(3) 41 ml of diisopropylamine were dissolved in dry tetrahydrofuran under argon gas stream. After cooling the solution to −10° C., 173 ml of a 1.66N n-butyl lithium solution was added dropwise to prepare a lithium diisopropylamide solution. After cooling the solution to a temperature of −60° C. or lower in a dry ice-acetone bath, a solution of 52 g of methyl phenylthioacetate in 100 ml of dry tetrahydrofuran was added to it dropwise under agitation. After agitating the mixture for 1 hour, a solution of 69 g of the compound of formula J, in 200 ml of dry tetrahydrofuran, was added dropwise at a temperature of −60° C. or lower. The reaction mixture was allowed to react for 20 minutes.

After adding dropwise 100 ml of a saturated ammonium chloride aqueous solution and then 50 ml of a sodium chloride aqueous solution to the reaction mixture, the resultant mixture was concentrated under reduced pressure to about 150 ml. The concentrate was extracted twice, each time with 200 ml of diethyl ether. After washing the ether phase with water and saturated sodium chloride, it was dried over anhydrous magnesium sulfate, was filtered, and was concentrated under reduced pressure to provide 130 g of an oily product.

Without purification, the oily product was mixed with 600 ml of acetic anhydride and 18 g of sodium acetic anhydride. The resultant mixture was heated under agitation for 1 hour in a oil bath preheated to 140° C. After allowing the reaction mixture to cool, it was poured onto 300 g of ice, 500 ml of diethyl ether were added, and sodium carbonate was added gradually under agitation, to neutralize the mixture. The ether phase was separated, was washed with water and saturated sodium chloride, was dried over anhydrous magnesium sulfate, and was evaporated to dryness to provide 90 g of (5R,8RS,2EZ)-methyl 8,11-diacetyloxy-5-isopropyl-3-phenylthio-2-undecenoate (the compound of formula K, wherein each of $R^3$ and $R^4$ is methyl group). The yield was 84%.

Analysis results:

Infrared spectrum (cm$^{-1}$): 2970, 2950, 2880, 1740, 1720, 1615, 1585, 1480, 1460, 1370, 1240, 1040, 1025, 790, 760, 760, 740, 690.

NMR spectrum (δ, ppm): 7.20 (m, 1H, H-3), 7.18 (s, 5H, -S-phenyl), 4.75 (m, 2H, H-11), 3.57 (s, 3H, ester-O-methyl), 2.4 (m, 2H, H-4), 1.98 (s, 6H, acetyl-methyl), 1.8-1.1 (10H), 0.87 (d, J=6 Hz, 6H, isopropyl-methyl).

(4) 90 g of the product of step 3 were dissolved in 1 liter of a 1% sodium methylate solution in methanol, and the resultant solution was refluxed for 1 hour. After the reaction mixture was allowed to cool, it was neutralized with a 2N hydrochloric acid solution and was concentrated under reduced pressure to about 150 ml. After adding 100 ml of water to the concentrate, the mixture was extracted three times, each time with 200 ml of diethyl ether. The ether phases were combined, washed with water and a saturated sodium chloride aqueous solution, and evaporated to dryness to provide 64 g of a crude product. Using hexane-ethyl acetate as an eluent, the crude product was subjected to chromatography with 200 g of silica gel. The fraction which eluted with hexane-ethyl acetate (1:2) was recovered and concentrated to provide 49 g of purified (5R,8RS,2EZ)-methyl 8,11-dihydroxy-5-isopropyl-2-phenylthio-2-undecenoate (the compound of formula L, wherein each $R^4$ is methyl group). The yield was 66%.

Analysis Results:

Infrared spectrum (cm$^{-1}$): 3375, 2975, 2900, 1730, 1720, 1610, 1590, 1480, 1470, 1440, 1390, 1375, 1255, 1045, 1035, 910, 745, 695.

NMR spectrum (δ, ppm): 7.20 (m, 1H, H-3), 7.13 (s, 5H, -S-phenyl), 4.22 (m, 1H, H-8), 3.53 (s, 3H, ester-methyl), 3.4 (m, 2H, H-11), 2.6-2.3 (m, 2H, H-4), 1.9-1.0 (10H), 0.85 (s, J=6.5 Hz, isopropyl-methyl).

(5) 25 g of the product obtained in step 4, 23 ml of triethylamine and 4.8 g of dimethylaminopyridine were dissolved in 150 ml of dry methylene chloride. After the solution was cooled to −22° C. with a dry ice-carbon tetrachloride bath, a solution of 20 g of para-toluenesulfonyl chloride in 20 ml of dry methylene chloride, was added to the solution dropwise under agitation, and the mixture was allowed to react at a temperature of −15° C. or lower for 2.5 hours. Then, 20 g of ice and 100 ml of a 1N hydrochloric acid solution were added to the reaction mixture, and the resultant mixture was extracted twice, each time with 200 ml of diethyl ether. The ether phases were combined, washed with a sodium carbonate aqueous solution and a saturated chloride aqueous solution, dried over anhydrous magnesium sulfate, filtered, and evaporated to dryness.

The residue was dissolved in a solution of 30 ml of dihydropyran in 120 ml of dry methylene chloride. Under agitation and cooling with ice, 1 g of pyridinium para-toluenesulfonate was added to the solution. Thereafter, the temperature of the reaction mixture was elevated to room temperature, and the mixture was allowed to react for 2 hours. The reaction mixture was then filtered using 50 g of "Florisil". After the "Florisil" was washed out with methylene chloride, the filtrate and the washing solution were combined, and the mixture was evaporated to dryness to provide 56 g of a crude product. Using n-hexane-ethyl acetate as an eluent, the crude product was subjected to column chromatography, using 600 g of silica gel. The fraction which eluted with n-hexane-ethyl acetate (8:2) was collected and was evaporated to dryness to provide 33 g of purified (5R, 8RS, 2EZ)-methyl 5-isopropyl-2-phenylthio-8-methoxy-11-methylsulfonyloxy-2-undecenoate (the compound of formula N, wherein each of $R^4$, $R^5$ and $R^6$ is methyl group). The yield was 81%.

(6) 4.6 g of sodium bistrimethylsilylamide were dissolved in 400 ml of dry dimethoxyethane under argon gas stream, and the mixture was refluxed. A solution of 12.0 g of the product of step 5, in 400 ml of dry dimethoxyethane, was added dropwise to the mixture under reflux, over 40 minutes. Thereafter, the reaction mixture was immediately cooled to room temperature, 5 ml of a saturated ammonium chloride aqueous solution were added thereto, and the resultant mixture was concentrated under reduced pressure to 100 ml.

The concentrate was extracted twice, each time with 150 ml of diethyl ether. The ether phases were combined, washed with water and a saturated sodium chloride aqueous solution, dried over anhydrous magnesium sulfate, and evaporated to dryness to provide 9.3 g of a crude cyclization product. Using n-hexane-ethyl acetate as an eluent, the crude product was subjected to column chromatography using 100 g of silica gel. The fraction which eluted with n-hexane-ethyl acetate (85:15) was collected and evaporated to dryness to provide 5.6 g of purified (1RS,2E,4S,7RS)-methyl 4-isopropyl-1-phenylthio-7-tetrahydropyranyloxy-2-cyclodecenecarboxylate (the compound of formula O, wherein each $R^4$ and $R^6$ is methyl group). The yield was 62%. The above operations were repeated three times, thereby obtaining a total of 16.8 g of the product.

Analysis Results:

NMR spectrum (δ, ppm): 7.30 (s, 5H, -S-phenyl), 5.50 (m, 2H, H 2, 3), 4.52 (m, 1H, tetrahydropyran-6), 2.3-1.0 (m, 18H), 0.9 (m, 3H, isopropyl-methyl).

(7) 2.08 g of lithium aluminum hydride were suspended in 600 ml of dry diethyl ether. While stirring the suspension and cooling it with ice, 16.3 g of the cyclized product of step 6 were added dropwise, over 10 minutes. After agitating the mixture for 1 hour, 3 ml of a 15% sodium hydroxide aqueous solution were added, dropwise, to the reaction mixture. The resultant mixture was filtered through a Buchner funnel and the precipitate on the funnel was washed with tetrahydrofuran. The filtrate and the washing solution were combined. The resultant mixture was washed with a saturated sodium chloride aqueous solution, was dried over anhydrous magnesium sulfate, was filtered, and was evaporated to dryness to provide 15.6 g of a desired product (the compound of formula P, wherein $R^6$ is methyl group). The yield was quantitative.

The product was mixed with 90 ml of pyridine, 2.3 g of dimethylaminopyridine, and 250 ml of dry tetrahydrofuran. While agitating the mixture and cooling it with ice, a solution of 8.7 g of benzoyl chloride in 30 ml of pyridine was added dropwise over 20 minutes. After the temperature of the mixture was elevated to room temperature, the reaction mixture was allowed to react under agitation overnight. The reaction mixture was poured onto ice water and was extracted twice, each time with 200 ml of ether. After the ether phases were combined and washed with a saturated sodium chloride aqueous solution, it was concentrated under reduced pressure to remove pyridine. After adding 100 ml of water to the residue and extracted with 300 ml of ether, the ether phase was washed three times with a copper sulfate aqueous solution. The ether phase was further washed with water and a saturated sodium chloride aqueous solution, was dried over anhydrous magnesium sulfate, was filtered, and was concentrated to provide about 20 g of a crude product.

After adding 50 ml of benzene to the crude product, reduced pressure concentration was performed twice. The concentrate was dissolved in 200 ml of methanol, 20 g of "Dowex 50W" ($H^+$ type) (an ion-exchange resin available from Dow Chemical Co.) were added to the solution, and the resultant mixture was stirred at 40° C. for 3 hours. After the ion-exchange resin was removed by filtering, the reaction mixture was evaporated to dryness to provide 16.5 g of a crude product. Using n-hexane-ethyl acetate as an eluent, the crude product was subjected to column chromatography using 100 g of silica gel. The fraction which eluted with n-hexane-ethyl acetate (8:2) was recovered, and evaporated to dryness to provide 12.7 g of a desired compound (the compound of formula Q, wherein $R^6$ is methyl group and $R^7$ is acetyl group). The yield was 81%.

(8) 14 g of naphthalene were dissolved in 400 ml of dry tetrahydrofuran under argon gas stream, and 2.3 g of fine metallic sodium were added to the solution. The mixture was allowed to react at room temperature for 4 hours to completely dissolve the sodium and to prepare a dark green solution of sodium naphthalenide. The resultant solution was cooled to −70° C. in a dry ice-acetone bath. A solution of 7.5 g of the product of step 7, in 50 ml of dry tetrahydrofuran, was added at once to the cooled solution under agitation, and the mixture was allowed to react for 5 minutes. A saturated ammonium chloride aqueous solution was added to the mixture until the color of the solution disappeared.

After concentrating the mixture under reduced pressure, 10 ml of water were added to the mixture and the resultant mixture was extracted twice, each time with 50 ml of diethyl ether. The ether phases were combined, washed with water and a saturated sodium chloride aqueous solution, dried over anhydrous magnesium sulfate, and evaporated to dryness. Using n-hexane-ethyl acetate as an eluent, the residue was subjected to column chromatography using 100 g of alumina (activity: II). After eluting naphthalene with n-hexane-ethyl acetate (95:5), the fraction which eluted with n-hexane-ethyl acetate (8:2) was recovered and was evaporated to dryness to provide 12.8 g of the compound according to the present invention, i.e., purified (1RS,4S,5E)-4-isopropyl-7-methylene-5-cyclodecen-1-ol (the compound of formula 1). The yield was 80%.

Analysis Results:
Specific rotation $[\alpha]_D^{22}$ −253° (c=1.85, n-hexane)
Infrared spectrum ($cm^{-1}$): 3375, 3100, 2980, 2960, 1755 (W), 1730 (W), 1640, 1615, 1470, 1450, 1390, 1375, 1315, 1240, 1180, 1060, 1040, 995, 945, 890.
NMR spectrum ($\delta$, ppm): 5.98 (d, J=16 Hz, 1H, H-6), 5.50 (dd, J=16 Hz, 10 Hz, 0.5H, H-5), 5.25 (dd, J=16 Hz, 9 Hz, 0.5H, H-5'), 4.77 (brs, 2H, exomethylene), 3.83 (m, 0.5H, H-1), 3.55 (m, 0.5 H, H-1'), −2.26 (m, 3H, H-4, 8), 2.0-1.0 (10H), −0.88 (m, 6H, isopropyl-methyl).

EXAMPLE 2

Synthesis of Optically Active Periplanone-B (1) 2.16 g of the compound of the invention, obtained in Example 1, were dissolved in a suspension of 6.3 g of chromic anhydride, 9.5 ml of pyridine, and 10 g of Molecular Sieves 3A in 160 ml of dry methylene chloride. The mixture was stirred at room temperature for about 30 minutes. Thereafter, 200 ml of diethyl ether were added to the reaction mixture, and the resultant mixture was filtered using 20 g of "Florisil". After the "Florisil" was washed with diethyl ether, the filtrate and the washing solution were combined and the resultant mixture was evaporated to dryness to provide 2.8 g of a crude product. Using n-hexane-ethyl acetate as an eluent, the product was subjected to column chromatography using 100 g of alumina (activity: II). The fraction which eluted with n-hexane-ethyl acetate (97:3) was recovered, and was evaporated to dryness to provide 2.26 g of purified (4S,5E)-4-isopropyl-7-methylene-5-cyclodecen-1-one. The yield was 86%.

Analysis Results:
Specific rotation $[\alpha]_D^{22}$ −362° (c=1, n-hexane).
Infrared spectrum ($cm^{-1}$): 3100, 2980, 2900, 1715, 1650 (W), 1615, 1465, 1430, 1390, 1370, 1330, 1260, 1215, 1185, 1155, 1120, 1095, 1055, 1010, 985, 880, 600.
NRM spectrum ($\delta$, ppm): 5.98 (d, J=16 Hz, 1H, H-6), 5.10 (dd, J=16 Hz, 10 Hz, 1H, H-5), 4.76 (s, 2H, exomethylene), 2.6-1.0 (12H), 0.85 (d, J=6.5 Hz, 3H, isopropyl-methyl), 0.78 (d, J=6.5 Hz, 3H, isopropyl-methyl).

(2) After dissolving 2.7 ml of hexamethyldisilazane (HMD) in 50 ml of dry tetrahydrofuran under argon gas stream, 7.3 ml of a 1.72N n-butyl lithium solution in n-hexane were added dropwise to prepare a lithium-bis-trimethylsilylamide solution. After cooling the solution to −70° C., a solution of 2.0 g of the product of step 1, in 5 ml of dry tetrahydrofuran, was added dropwise under stirring and the resultant solution was agitated for 1 hour. The reaction mixture was added at once under agitation to a precooled (with ice) solution of 3.16 g of phenylthiobenzenesulfonate in 40 ml of dry tetrahydrofuran. After stirring the mixture for 10 minutes, 5 ml of a saturated sodium chloride aqueous solution were added to the reaction mixture, and this mixture was concentrated under reduced pressure. After adding 50 ml of water to the residue, the solution was extracted three times, each time with 50 ml of diethyl ether. The ether phases were combined, sequentially washed with water, a saturated sodium bicarbonate aqueous solution and a saturated sodium chloride aqueous solution, dried over anhydrous magnesium sulfate, and evaporated to dryness to provide (4S,5E)-4-isopropyl-7-methylene-10-phenylthio-5-cyclodecen-1-one.

Without purification, the resultant product was stirred at room temperature in a solvent mixture of 35 ml of water and 170 ml of methanol together with 3.5 g of sodium periodate, for 20 hours. The reaction mixture was filtered, and the precipitate was washed with methanol. The filtrate and the washing solution were combined, and the mixture was concentrated under reduced pressure. Then, 50 ml of water were added to the concentrate, and the mixture was extracted three times, each time with 50 ml of diethyl ether. The ether phases were combined, sequentially washed with water, a saturated sodium bicarbonate aqueous solution and a saturated sodium chloride aqueous solution, dried over anhydrous potassium carbonate, and evaporated to dryness to provide 3.1 g of a crude product.

Using n-hexane-ethyl acetate as an eluent, the crude product was subjected to column chromatography using 200 g of alumina (activity: II). The fraction which eluted with the n-hexane-ethyl acetate (3:2) was recovered and was evaporated to dryness to provide 2.26 g of purified (4S,5E)-4-isopropyl-7-methylene-10-phenylsulfinyl-5-cyclodecen-1-one. The yield was 83%.

(3) After dissolving 2.6 g of the product of step 2 in 200 ml of toluene, 2.5 g of calcium carbonate were added to the solution and the mixture was refluxed under nitrogen gas stream for 5 hours. The reaction mixture was filtered to remove calcium carbonate, and the filtrate was concentrated under reduced pressure to 5 ml. Then, 10 ml of hexane were added to the concentrate. Using n-hexane-ethyl acetate as an eluent, the mixture was subjected to column chromatography using 100 g of alumina (activity: II). The fraction which eluted with n-hexane-ethyl acetate (95:5) was recovered and was evaporated to dryness to provide 760 mg of purified (8S,2Z,6E)-8-isopropyl-5-methylene-2,6-cyclodecadiene-1-one. The yield was 47%.

Analysis Results:
NMR spectrum (δ, ppm): 5.88 (d, J=11 Hz, 1H, H-7), 5.77 (d, J=15 Hz, 1H, H-6), 5.45 (ddd, J=11.4 Hz, 10.7 Hz, 7 Hz, 1H, H-3), 5.32 (dd, J=15 Hz, 11 Hz, 1H, H-7), 4.87 (s, 1H, exomethylene), 4.80 (s, 1H, exomethylene), 3.69 (dd, J=12 Hz, 11 Hz, 1H, H-4), 2.57 (dd, J=12 Hz, 7 Hz, 1H, H-4'), 2.16 (m, 1H, H-10), 2.12 (m, 1H, H-8), 1.91 (dd, J=14 Hz, 5 Hz, 1H, H-10'), 1.54 (m, 2H, H-9), 1.45 (m, 1H, isopropyl-H), 0.89 (d, J=6.7 Hz, 3H, isopropylmethyl), 0.88 (d, J=6.7 Hz, 3H, isopropylmethyl).

(4) 730 mg of potassium hydride were suspended in 150 ml of dry tetrahydrofuran under argon gas stream. Under ice cooling and agitation, 9 ml of a 4N t-butylhydroperoxide solution in toluene was added to the mixture, which was then stirred for 15 minutes. A solution of 750 mg of the product of step 3, in 10 ml of dry tetrahydrofuran, was added dropwise to the mixture. After the temperature of the reaction mixture was elevated to room temperature, it was stirred for 1 hour. After the reaction completed, 10 g of ice were added to the mixture, and the resultant mixture was extracted four times, each time with 100 ml of diethyl ether. The ether phases were combined, washed with a sodium sulfite aqueous solution, and concentrated under reduced pressure.

After adding 50 ml of water to the concentrate, it was extracted twice, each time with 100 ml of diethyl ether. The ether phases were combined, sequentially washed with water, a saturated sodium bicarbonate aqueous solution and a saturated sodium chloride aqueous solution, dried over anhydrous potassium carbonate, and evaporated to dryness to provide a crude product.

Using n-hexane-ethyl acetate as an eluent, the crude product was subjected to column chromatography using 100 g of alumina (activity: II). The fraction which eluted with n-hexane-ethyl acetate (9:1) was recovered and was evaporated to dryness to provide 660 g of purified (4S,5E,9R,10R)-epoxy-4-isopropyl-7-methylene-5-cyclodecen-1-one. The yield was 82%.

Analysis Results:
Melting Point: 39°-41° C.
Specific rotation: $[\alpha]_D^{23} -347°$ (c=1.30, n-hexane).
Infrared spectrum (cm$^{-1}$): 3100, 2980, 2950, 2890, 1725, 1655, 1615, 1470, 1445, 1415, 1370, 1325, 1255, 1205, 1185, 1120, 1085, 1065, 1025, 980, 895, 860, 815, 800.

NMR spectrum (δ, ppm, 500 MHz, in benzene-d$_6$): 5.74 (d, J=16 Hz, 1H, H-6), 5.08 (dd, J=10 Hz, 16 Hz, 1H, H-5), 4.84 (s, 1H, exomethylene), 4.82 (s, 1H, exomethylene), 3.11 (d, J=5 Hz, 1H, H-10), 2.86 (ddd, J=4 Hz, 5 Hz, 10 Hz, 1H, H-9), 2.60 (dd, J=3 Hz, 13 Hz, 1H, H-8), 2.44 (dd, J=10 Hz, 13 Hz, 1H, H-8'), 2.16 (m, 1H, H-4), 1.93 (dd, J=12 Hz, 16 Hz, 1H, H-2), 1.72 (dd, J=7 Hz, 1H, H-2'), 1.45 (m, 1H, isopropyly-H), 1.37 (m, 2H, H-3), 0.86 (d, J=6 Hz, 3H, isopropylmethyl), 0.83 (d, J=6 Hz, 3 H, isopropyl-methyl).

(5) 0.38 ml of HMD were dissolved in 16 ml of dry tetrahydrofuran under the stream of argon gas. Under cooling with ice, 1.02 ml of a 1.72N n-butyl lithium solution in n-hexane were added dropwise to prepare a lithium bistrimethylsylylamide solution. After the solution was cooled to −70° C., a solution of 300 mg of the product obtained in step 4, in 4 ml of dry tetrahydrofuran, was added dropwise under agitation and the resultant mixture was stirred for 30 minutes. 5.8 ml of a 0.33N phenylselenyl bromide solution in tetrahydrofuran were added to the reaction mixture under agitation and the mixture was allowed to react for 10 minutes. The reaction mixture was poured onto ice and was extracted twice, each time with 50 ml of diethyl ether. The ether phases were combined, washed with water and saturated sodium chloride, dried over anhydrous potassium carbonate, and evaporated to dryness to provide a crude product.

Using n-hexane-ethyl acetate as an eluent, the crude product was subjected to column chromatography using 40 g of alumina (activity: II). The fraction which eluted with n-hexane-ethyl acetate (97:3) was recovered and was evaporated to dryness to provide 416 mg of a purified selenide compound. The yield was 85%.

(6) After 200 mg of the selenide compound of step 5 were dissolved in 1 ml of tetrahydrofuran, 0.5 ml of a 35% hydrogen peroxide aqueous solution were added to the mixture under cooling with ice and 2 droplets of pyridine were added to the mixture. The temperature of the mixture was elevated to room temperature, and the mixture was allowed to react for 1 hour under agitation. After the reaction was terminated, the reaction mixture was diluted with 10 ml of ethyl acetate, was cooled with ice, and 5 ml of a 10% sodium sulfite aqueous solution were added thereto. The organic phase was separated, was washed with water and a saturated sodium chloride aqueous solution, was dried over anhydrous potassium carbonate, and was evaporated to dryness to provide 208 mg of unstable (4S,5E,9R,10R)-9-epoxy-4-isopropyl-7-methylene-2-phenyl selenyl-5-cyclodecen-1-one. The yield was 88%.

(7) 109 mg of sodium acetate were suspended in 2.7 ml of dry tetrahydrofuran, and 100 mg of the product of step 6 were added to the suspension. While the resultant mixture was cooled with ice and stirred, 0.14 ml of acetic anhydride were added dropwise, and the temperature was immediately elevated to room temperature. The mixture was then stirred for 2 hours. After 2 ml of methanol were added to the reaction mixture and stirred for 5 minutes, 2 ml of a saturated potassium carbonate aqueous solution were added and the mixture was further stirred for 2 hours. The reaction mixture was extracted twice, each time with 20 milliliters of diethyl ether. The ether phase were combined, washed with water and a saturated sodium chloride aqueous solution, dried over anhydrous potassium carbonate, and evaporated to dryness to provide 54 mg of a crude product.

Using n-hexane-ethyl acetate as an eluent, the crude product was subjected to column chromatography using 20 g of alumina (activity: II). The fraction which eluted with n-hexane-ethyl acetate (98:2) was recovered and was evaporated to dryness to provide 26 mg of purified (3S,4E,8R,9R)-8-epoxy-3-isopropyl-6-methylene-10-oxo-4-cyclodecen-1-one. The yield was 60%.

Analysis results:
Specific rotation: $[\alpha]_D^{23} - 424°$ (c=0.44, n-hexane).
Infrared spectrum (cm$^{-1}$): 3100, 2980, 2950, 2900, 1725, 1710, 1645, 1615, 1470, 1455, 1430, 1410, 1390, 1375, 1305, 1260, 1245, 1170, 1115, 1075, 1045, 1030, 1010, 985, 960, 925, 905, 880, 850, 800, 755.

NMR spectrum (δ, ppm, 500 MHz, in benzene-d$_6$): 5.65 (d, J=16 Hz, 1H, H-5), 5.14 (dd, J=11 Hz, 16 Hz, 1H, H-4), 4.76 (s, 1H, exomethylene), 4.71 (s, 1H, exomethylene), 4.34 (d, J=5 Hz, 1H, H-9), 3.33 (dd, J=10 Hz, 11 Hz, 1H, H-7), 2.78 (ddd, J=3 Hz, 5 Hz, 10 Hz, 1H, H-8), 2.52 (dd, J=3 Hz, 11 Hz, 1H, H-7'), 2.16 (dd, J=10 Hz, 14 Hz, 1H, H-2), 2.14 (dd, J=6 Hz, 10 Hz, 1H, H-2'), 1.84 (m, 1H, H-3), 1.21 (m, 1H, isopropyl-H), 0.67 (d, J=7 Hz, 3H, isopropyl-methyl), 0.66 (d, J=6 Hz, 3H, isopropyl-methyl).

(8) 22 mg of trimethylsulfonium iodide, 1 ml of dimethylsulfoxide, and 3 mg of sodium hydride were stirred under argon gas stream to prepare a solution of dimethylsulfoniummethylide. This solution was added dropwise under ice cooling to a solution of 25 mg of the product obtained in step 7, in 1 ml of tetrahydrofuran, and the mixture was allowed to react for 5 minutes. After adding 1 ml of water to the reaction mixture, the mixture was extracted with 15 ml of diethyl ether. The ether phase was washed twice with water, was washed with a saturated sodium chloride aqueous solution, was dried over anhydrous potassium carbonate, and was evaporated to dryness to provide a crude product.

Using n-hexane-ethyl acetate as an eluent, the crude product was subjected to column chromatography using 1 g of alumina (activity: II). The fraction which eluted with n-hexane-ethyl acetate (98:2) was recovered and was evaporated to dryness to provide 14.0 mg of purified crystals of optically active periplanone-B. The yield was 53%.

Analysis results:
Melting Point: 47°–50° C.
Specific rotation: $[\alpha]_D^{23} - 667°$ (c=0.13, n-hexane).
Infrared spectrum (cm$^{-1}$): 3075, 2950, 2925, 2870, 1705, 1695, 1655 (W), 1645 (W), 1605, 1445, 1420, 1380, 1360, 1325, 1300, 1270, 1245, 1225, 1160, 1110, 1100, 970, 935, 905, 890, 850, 835, 815, 805, 790, 720, 710, 695.

NMR spectrum (δ, ppm, 500 MHz, in carbon disulfide): 5.91 (brd, J=16 Hz, 1H, H-5), 5.78 (dd, J=16 Hz, 10 Hz, 1H, H-6), 5.02 (brs, 1H, H-15), 4.87 (brs, 1H, H-15'), 3.52 (d, J=4 Hz, 1H, H-1), 2.84 (d, J=6 Hz, 1H, H-14), 2.68 (ddd, J=8 Hz, 6 Hz, 4 Hz, 1H, H-2), 2.63 (d, J=6 Hz, 1H, H-14'), 2.58 (d, J=12 Hz, 2H, H-3), 2.55 (dd, J=11.5 Hz, 10 Hz, 1H, H-8), 2.06 (m, 1H, H-7), 2.04 (dd, J=11.5 Hz, 5.5 Hz, 1H, H-8'), 1.56 (m, 1H, H-11), 0.92 (d, J=6.5 Hz, 3H, isopropyl-methyl), 0.87 (d, J=6.5 Hz, 3H, isopropyl-methyl).

Industrial Applicability

As has been described above, the compound of the present invention can be manufactured as an optically active substance by a method which is suitable for the manufacture on an industrial scale, and can be manufactured at a high yield. Therefore, the compound of the present invention is very useful as an intermediate in the manufacture of optically active periplanone-B on an industrial scale.

We claim:

1. 4-isopropyl-7-methylene-5-cyclodecen-1-ol represented by a formula:

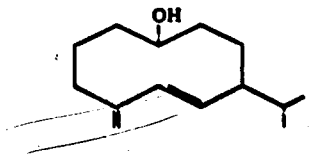

2. The compound according to claim 1, which is (1RS,4S,5E)-4-isopropyl-7-methylene-5-cyclodecen-1-ol.

* * * * *